United States Patent [19]
Devlin et al.

[11] Patent Number: 5,238,002
[45] Date of Patent: Aug. 24, 1993

[54] DISPOSABLE BIOPSY FORCEPS

[75] Inventors: Peter J. Devlin, Billerica; Barry D. Weitzner, Acton, both of Mass.; Thomas Watson, Hooksett, N.H.

[73] Assignee: C. R. Bard, Inc., Murray Hill, N.J.

[21] Appl. No.: 895,321

[22] Filed: Jun. 8, 1992

[51] Int. Cl.⁵ .............................. A61B 10/00
[52] U.S. Cl. ........................ 128/751; 606/205
[58] Field of Search .......... 128/749, 751, 754; 606/205-208

[56] References Cited

U.S. PATENT DOCUMENTS

| | | | |
|---|---|---|---|
| 391,532 | 10/1888 | Hoffman . | |
| 430,849 | 6/1890 | Groth . | |
| 2,060,366 | 10/1935 | Dunlap . | |
| 3,895,636 | 7/1975 | Schmidt | 606/205 |
| 4,200,111 | 4/1980 | Harris | 128/751 |
| 4,427,014 | 1/1984 | Bel et al. | 128/751 |
| 4,721,116 | 1/1988 | Schintgen et al. | 606/208 |
| 4,881,550 | 11/1989 | Kothe | 128/752 |
| 4,887,612 | 12/1989 | Esser et al. | 128/751 |
| 5,052,402 | 10/1991 | Bencini et al. | 128/751 |
| 5,082,000 | 1/1992 | Picha et al. | 128/751 |
| 5,133,727 | 7/1992 | Bales et al. | 128/751 |
| 5,141,519 | 8/1992 | Smith et al. | 128/751 |

Primary Examiner—Max Hindenburg
Attorney, Agent, or Firm—Wolf, Greenfield & Sacks

[57] ABSTRACT

A disposable biopsy forceps includes an elongate tubular member having proximal and distal ends. Manually operated actuating means is mounted to the proximal end of the flexible tubular member. A biopsy jaw assembly is mounted to the distal end of the tubular member and is operatively connected to the actuating means by a control wire extending through the tubular member.

8 Claims, 3 Drawing Sheets

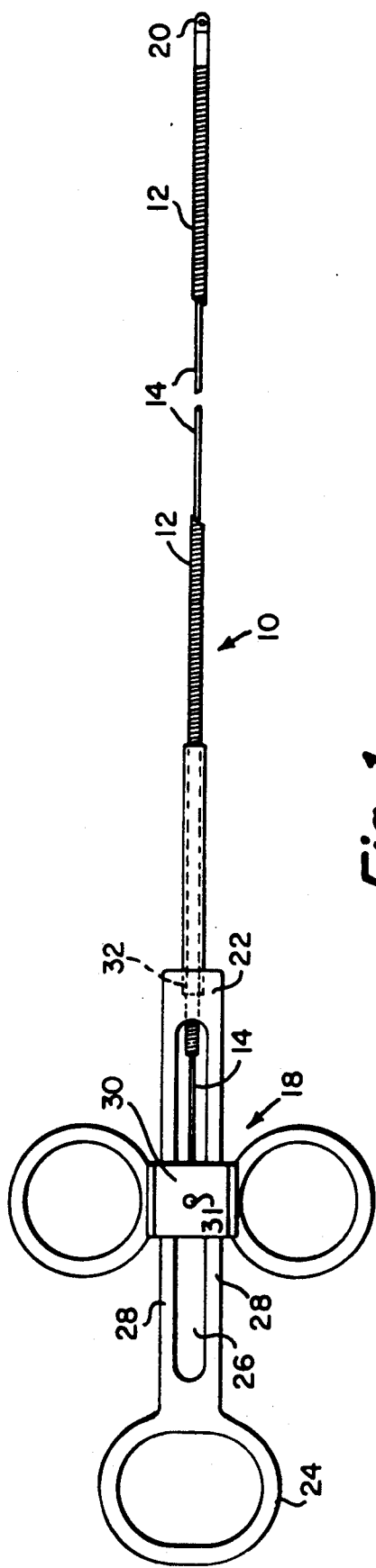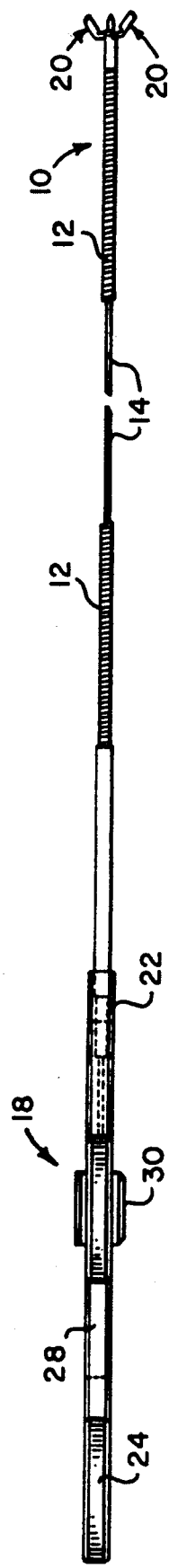

5,238,002

DISPOSABLE BIOPSY FORCEPS

FIELD OF THE INVENTION

The invention relates to biopsy forceps for taking small internal tissue samples from a patient.

BACKGROUND OF THE INVENTION

When making an endoscopic examination of a particular site in a patient s body, it is common for the physician to take at least one tissue sample from that site for analysis. A variety of such devices for taking of small tissue samples are in use. In general, such biopsy devices include a small diameter elongate catheter like instrument adapted to be passed through a lumen in the endoscope, the device being longer than the endoscope so that its distal end can extend out of the distal end of the endoscope. The distal end of the device typically is provided with a pair of sharp jaws that can be opened and closed to cut and draw away a small sample of tissue to be investigated. The opening and closing of the jaws is controlled manually by the physician by manipulating controls at the proximal end of the device.

Such endoscopic biopsy procedures involve repeated insertion and removal of the device through the narrow endoscope channel when it is necessary to take multiple biopsies. The device must be sufficiently rugged to withstand such repeated use yet must be constructed so that it will not cause damage to any of the parts of the endoscope as it is advanced through the endoscope channel.

Among the difficulties presented with such devices is that they typically are relatively expensive, partly because of the intricate work required to manufacture the miniature jaws and jaw actuating mechanisms. Additionally, the cutting edges of the jaw tend to become dull with use and require periodic sharpening, a procedure that involves considerable skill and a high degree of care because of the miniature size of the jaws. Very slight errors in sharpening procedure can impair seriously the effectiveness of the jaws. Often, it is only possible to sharpen such a device a few times before its dimensions are so changed that it is no longer effective. When that occurs, it is common practice to replace the entire device. Also among the difficulties presented by such endoscopic biopsy devices is that they are difficult to clean and sterilize. The jaw mechanisms define numerous crevices. Additionally, the elongate body of the device is made from a highly flexible tightly wound helical coil which provides numerous crevices for retaining debris or contaminants and the like.

It is believed that there is a need for a low cost, simple, disposable endoscopic biopsy device. It is among the general objects of the invention to satisfy that need.

SUMMARY OF THE INVENTION

The device includes an elongate flexible tubular catheter shaft and a control wire that extends through the catheter and is connected at its proximal end to an actuation means by which the physician may pull or push on the wire. The distal end of the device carries a pair of jaws each of which has at its end a sharp rimmed cup so that when the jaws are brought together, they may sever and retain a sample of tissue. Unlike the prior art biopsy devices, the present invention, embodies a simple and inexpensive arrangement for the biopsy jaws that is free of complex linkages and multiple hinge points. The present invention has only a single hinge point It is among the general objects of the invention to provide endoscopic biopsy devices having biopsy jaw arrangements that are of relatively simple inexpensive design.

Another object of the invention is to provide an endoscopic biopsy device of sufficiently low cost as to be disposable.

A further object of the invention is to provide an endoscopic biopsy device having a simplified, positive means for opening and closing its jaws.

Another object of the invention is to provide an endoscopic biopsy device in which the jaws, when closed, remain in the closed position until opened by the user.

DESCRIPTION OF THE DRAWINGS

The foregoing and other objects and advantages of the invention will be appreciated more fully from the following further description thereof, with reference to the accompanying drawings wherein:

FIG. 1 is a fragmented, partly broken away illustration of an endoscopic biopsy device in accordance with the present invention;

FIG. 2 is a side view of the device as shown in FIG. 1 with the biopsy jaws in an open configuration;

DESCRIPTION OF THE PREFERRED EMBODIMENT

Figure 3:
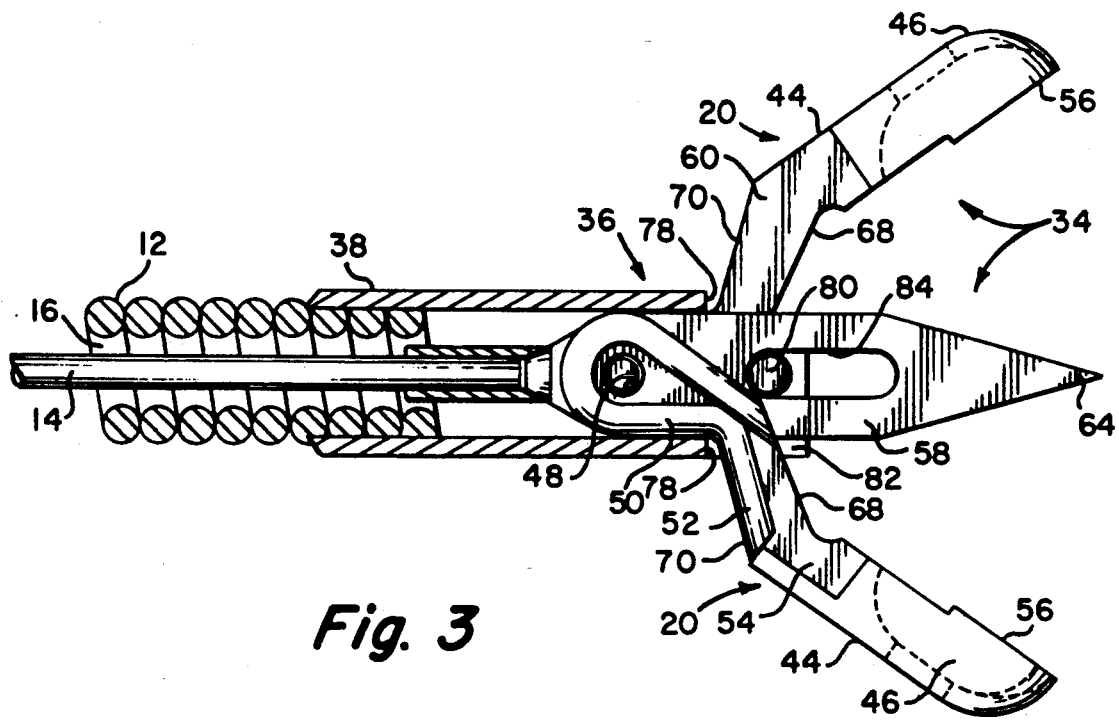
FIG. 3 is an enlarged sectional illustration of the distal end of the device showing the biopsy jaws in an open configuration.

As shown in FIGS. 1 and 2, the invention is embodied in a biopsy device having an elongate flexible tubular shaft 10 which may be formed from a stainless steel helical coil 12. A control wire 12, that also may be formed from stainless steel, extends through the lumen 16 (see FIG. 3) defined by the helical coil 12. The control wire 14 is connected to an actuating means 18 at the proximal end of the device by which the physician controls its operation. A pair of biopsy jaws 20 is carried at the distal end of the shaft 10. The jaws 20 are operably associated with the control wire 14 so that they may be closed (FIGS. 4, 5) or opened (FIGS. 2, 3) by operation of the control wire 14. When the jaws 20 are closed, they define a diameter substantially the same as the outer diameter of the shaft 10 so that the entire device will fit slidably through the channel of the endoscope. For ease in description, directions or locations toward the longitudinal axis of the device will be referred to as "inward" while directions away from the longitudinal axis will be referred to as outward. Thus, the biopsy jaws may be considered to swing inwardly when they close and outwardly when they open.

The dimensions of the channel in the endoscope will vary for different types of endoscopes. For example, endoscopes used in gastrointestinal environments typically have a biopsy channel 2.8 mm in diameter whereas endoscopes for pulmonary use typically have a biopsy channel 2.0 mm in diameter. Additionally, the lengths of such endoscopes varies according to their use. Pulmonary endoscopes are shorter than gastrointestinal endoscopes. By way of further example, the shaft 10 of the present invention may be of the order of between 0.070" to 0.080" in diameter and may be between 100 cm to 240 cm in length, depending on the type and size of the endoscope with which it is to be used. Other lengths and diameters may be appropriate for other types of endoscopes which may have different lengths and channel sizes. It may be desirable, in use, to coat the outer surface of the coil 12 with a lubricious material.

The diameter of the control wire 14 depends on the length of the device and, possibly, on the type of tissue which the device will be used to sample. The stiffness of the control wire is a function of its diameter. Preferably, the control wire usable for the particular type of endoscope should be the smallest diameter that will operate the jaws 20 so as not to adversely affect the flexibility of the device. By way of example, we have found that a control wire as small as 0.016" diameter may be effective to operate the jaws in a device 100 cm to 240 cm long. The control wire preferably is coated with Teflon (polytetrafluoroethylene) to enhance its ability to slide in the coil 12.

As shown in FIGS. 1 and 2, the actuating means 18 includes a stationary member 22 that is attached to the proximal end of the coil 12. The stationary member 22 preferably is provided with a thumb socket 24. The stationary member 22 also is provided, with a longitudinally extending slot 26 that separates and defines a pair of parallel rails 28. A movable slide 30 is provided with a pair of finger holes and is slidably mounted to the rails 28. The proximal end of the coil 12 extends through an opening 32 in the stationary member 22 and guides the control wire 14 to a point of attachment 31 on the slide 30. From the foregoing, it will be appreciated that the proximal end of the device can be operated with one hand, to pull proximally on the control wire 14 or to push it distally. The device is arranged so that pushing on the wire opens the jaws 20 and pulling on the wire 14 causes the jaws 20 to close.

As shown in FIGS. 3-7, the device includes a jaw and barb assembly, indicated generally at 34 (FIGS. 3 and 7), and an asymmetrical tubular clevis indicated generally at 36. The clevis 36 has a proximal end 38 that is securely attached to the distal end of the coil 12 and a distal end having a pair of slots 40, 42 arranged asymmetrically as described in further detail below.

The jaw and barb assembly 34 includes the biopsy jaws 20 which, in turn, have arms 44, cutting cups 46 at the outer ends of the arms 44 and are pivoted to each other their inner ends at a pivot pin 48. Each of the arms may be considered as having a proximal segment 50, an outwardly offset intermediate segment 52 and a distal segment 54, the cutting cup 46 for that jaw being integrally formed with the distal segment. The jaws may be machined or may be formed by other techniques such as metal injection molding. The arms 44 and cups 46 are formed from stainless steel. The rim of each cup 46 defines a sharpened edge 56. The pivot pin 48 connects the arms at their proximal segments 50. The intermediate segment 52 is offset so that the distal segment 54 and its associated cutting cup 56 will be disposed outwardly of the proximal segment 50.

The device also may include a barb 58 that extends longitudinally of the device. The barb 58 may be formed from a flat sheet of stainless steel interposed between the flat inwardly facing surfaces 60 of the proximal segments 50 of the arms 44. The barb 58 has a proximal end 62 through which the pivot pin 48 is passed and a distal end 64 which is sharpened to a point. The proximal end 62 of the barb is secured, as by an integral extension 66 to the distal end of the control wire 14. The intermediate segment 52 of each of the arms also may be considered as having an inwardly facing camming surface 68 and an outwardly facing camming surface 70 which function in the manner described below.

Figure 4:
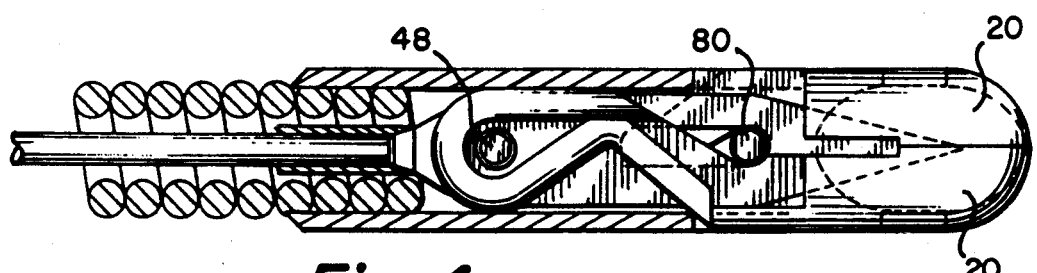
FIG. 4 is an illustration similar to FIG. 3 with the biopsy jaws in a closed configuration.
Figure 5:
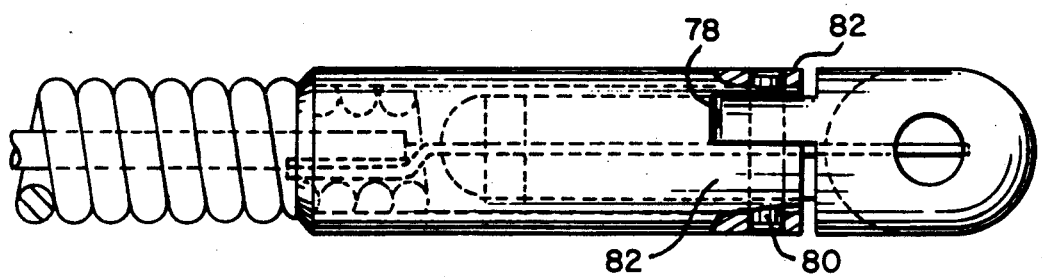
FIG. 5 is an illustration of the distal end of the device as seen along the line 5—5 of FIG. 4.
Figure 6:
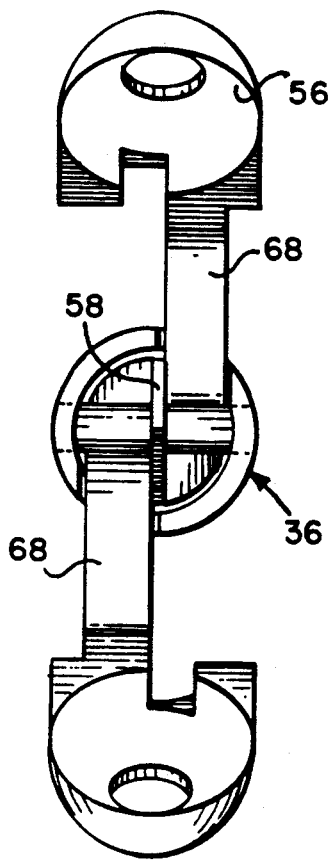
FIG. 6 is an end view of the device as shown in FIG. 3 with the jaws open as seen from the right of FIG. 3.
Figure 8:
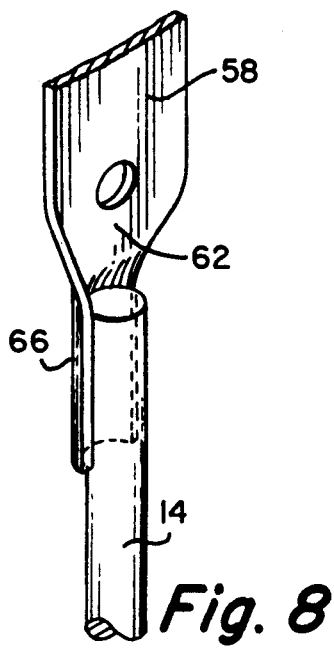
FIG. 8 is a further enlarged illustration of the connection between the control wire 14 and the jaw and barb assembly.
Figure 7:
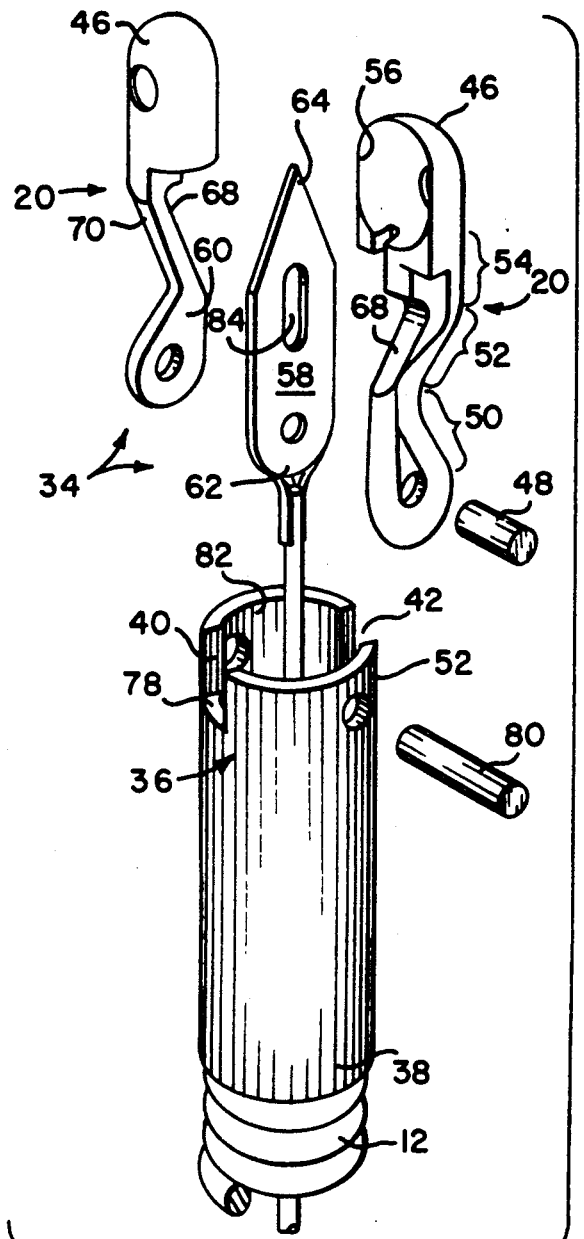
FIG. 7 is an exploded illustration of the components at the distal end of the device.

The distal portion of the asymmetrical tubular clevis 36 is arranged to receive the proximal and intermediate segments 50, 52 of the arms when the biopsy jaws are in their closed configuration as suggested in FIGS. 4 and 5. The distal end of the tubular clevis 36 includes the pair of asymmetrically arranged slots 40, 42. Each of the slots 40, 42 is arranged to receive one of the arms 44, the width of each slot being just sufficient to receive the corresponding width of one of the arms 44. Engagement of the sides of the arms 44 with the facing sides of the slots 40, 42 stabilizes the arms 44 and guides them closely in inward and outward movement with minimal side by side movement. This further assures effective cooperative cutting by the inwardly facing sharp edges 56 of the cutting cups 46 when the cups are brought together.

Each of the slots 40, 42 is generally U shaped and includes a bottom surface 78. The tubular clevis also includes a camming member in the form of a pin 80 attached at its ends to the distal most end walls 82 of the tubular clevis 36. The pin 80 passes through a longitudinally extending slot 84 in the barb 58 and serves to stabilize the barb in a longitudinally extending position. The slot 84 is sufficiently long to permit the barb 58 to move lengthwise of the shaft 10 together with the jaws 20 as the control wire 14 is operated. The pin 80 is disposed with respect to the inner cam surfaces 68 of the arms 44 so that when the control wire 14 is advanced distally, the distally advancing arms 48 will be urged outwardly as the inner cam surfaces 68 advance against the pin 80. In order to close the jaws, the control wire 14 is retracted proximally. In that motion, the outer cam surfaces 70 bear and slide against the bottom surfaces 78 of the slots 40, 42 to swing the arms 44 inwardly. The foregoing arrangement results in closure of the cups with relatively little longitudinal motion thereby enhancing a clean cut with minimal tearing of tissue. Thus, the jaws are caused to open by distal movement of the control wire and cooperation of the pin 80 with the inner cam surfaces while closure of the device is effected by proximal retraction of the control wire and resulting cooperation of the outer cam surfaces with the bottom surfaces 78 of the clevis.

The sharp tip of the barb 58 serves to permit the device, with open jaws, to be brought firmly against the surface of tissue to be biopsied and by embedment in the tissue to maintain a fixed position of the jaws with respect to the tissue, even if the tissue is in motion, as is often the case when sampling tissue from a living patient. The jaws then simply may be closed by pulling on the control wire 14, the barb retracting simultaneously with the closure motion.

From the foregoing, it will be appreciated that the invention provides an improved biopsy device having a simplified mechanism and including only a single pivot point. The device lends itself to relatively low cost manufacture and, therefore, is adaptable to disposable use. It should be understood, however, that the foregoing description of the invention is intended merely to be illustrative thereof and that other modifications, embodiments and equivalents may be apparent to those skilled in the art without departing from its spirit.

Having thus described the invention what we desire to claim and secure by Letters Patent is:

1. A biopsy device comprising:
    an elongate flexible tube having a proximal end and a distal end;
    a pair of biopsy jaws each having a proximal end and a distal end, the proximal ends of the biopsy jaws being pivoted to each other at a pivot for closing inward and opening outward movement;
    an actuating member extending through the tube and being connected at its distal end to the pivot, the actuating member being controllable from the proximal end of the device to be movable proximally or distally within the tube, the pivot being movable with the actuating member;
    the jaws having inner and outer camming surfaces;
    the distal end of the tube having members integrally therewith engageable, respectively, with the inner and outer camming surfaces of the jaws to cause the jaws to open when the actuating member is moved in one direction and to close when the actuating member is moved in the opposite direction.

2. A biopsy device as defined in claim 1 wherein each of the jaws further comprises:
    an arm having an inner segment, an outwardly offset intermediate segment extending from the distal end of the inner segment and a distal segment extending from the distal end of the intermediate segment;
    a biopsy cup attached to the distal segment of each arm.

3. A biopsy device as defined in claim 2 wherein the inner and outer camming surfaces are formed on the inner and outwardly facing surfaces of the intermediate segment.

4. A biopsy device as defined in claim 2 further comprising:
    the distal end of the tube being formed to define a pair of slots, each slot being associated with and adapted to receive a portion of one of the arms, the width of each slot corresponding substantially to the width of the arm associated with the slot thereby to enable the arm to move through the slot while providing lateral stability for the arm.

5. A biopsy device as defined in claim 4 wherein the camming members at the distal end of the tube comprise the bottom of the slots that receive the arms, said slot bottoms being engageable with the outer camming surfaces; and
    a transverse member mounted to the distal end of the tube generally parallel to the pivot axis, the transverse member being engageable simultaneous with the inwardly facing camming surfaces.

6. A biopsy device as defined in claim 2 wherein the proximal segments of the arms are received substantially fully within the distal end of the tube when the jaws are closed thereby locking the jaws in a closed configuration.

7. A biopsy device as defined in any one of claims 1-6 further comprising:
    a barb member comprising a flat elongate plate having a proximal end captured between the jaws and pivoted to the pivot pin, the barb plate having a distally extending sharpened end and a stabilizer for maintaining the barb in a longitudinally oriented attitude.

8. A biopsy device as defined in claim 7 wherein the stabilizer comprises an elongate slot formed in the plate, the slot receiving the transverse member in a lost motion connection.

* * * * *